(12) United States Patent
Taylor et al.

(10) Patent No.: US 12,268,796 B2
(45) Date of Patent: Apr. 8, 2025

(54) SYSTEM AND METHODS FOR SOFT-TISSUE AUGMENTATION

(71) Applicant: NuVista, LLC, Carlsbad, CA (US)

(72) Inventors: Alan G. Taylor, Memphis, TN (US); Bruce R. Lawrence, Oceanside, CA (US); Rebecca Hawkins Wahl, Escondido, CA (US)

(73) Assignee: TheraMicro, LLC, Memphis, TN (US)

( * ) Notice: Subject to any disclaimer, the term of this patent is extended or adjusted under 35 U.S.C. 154(b) by 1020 days.

(21) Appl. No.: 17/165,371

(22) Filed: Feb. 2, 2021

(65) Prior Publication Data

US 2021/0154367 A1 May 27, 2021

Related U.S. Application Data

(63) Continuation-in-part of application No. 15/987,732, filed on May 23, 2018, now Pat. No. 12,133,930.

(60) Provisional application No. 62/510,601, filed on May 24, 2017.

(51) Int. Cl.
*A61L 27/36* (2006.01)
*A61L 27/12* (2006.01)
*A61L 27/38* (2006.01)
*A61L 27/50* (2006.01)
*A61M 5/46* (2006.01)

(52) U.S. Cl.
CPC .......... *A61L 27/3608* (2013.01); *A61L 27/12* (2013.01); *A61L 27/3839* (2013.01); *A61L 27/50* (2013.01); *A61M 5/46* (2013.01); *A61L 2430/34* (2013.01)

(58) Field of Classification Search
CPC ........ A61L 27/26; A61L 27/025; A61L 27/18; A61L 27/20; A61L 27/362; A61L 27/3666; A61L 27/3695; A61L 27/54; A61L 2300/412; A61L 2400/06; A61L 2430/34; A61M 5/178; A61M 5/1782; A61M 5/46; A61M 5/002; A61M 2210/0606; A61M 2210/083; A61M 2210/08

See application file for complete search history.

(56) References Cited

U.S. PATENT DOCUMENTS

| | | | |
|---|---|---|---|
| 7,850,651 B2 * | 12/2010 | Allee | A61B 10/025 604/164.04 |
| 12,133,930 B2 * | 11/2024 | Taylor | A61M 5/178 |
| 2018/0339085 A1 * | 11/2018 | Taylor | A61L 27/18 |

FOREIGN PATENT DOCUMENTS

WO  WO-2008148071 A2 * 12/2008 ............ A61J 1/2096

OTHER PUBLICATIONS

Hoffman et al. (Laryngoscope, Apr. 2010, 120(4), pp. 769-776; doi: 10.1002/lary.20830). (Year: 2010).*

* cited by examiner

*Primary Examiner* — Aaron J Kosar
(74) *Attorney, Agent, or Firm* — Rutan & Tucker LLP; Hani Z. Sayed

(57) ABSTRACT

Provided herein is an injectable composition including, in some embodiments, a soft-tissue augmenting agent and a vehicle for the soft-tissue augmenting agent formulated for augmenting one or more soft tissues of a human or animal. Also provided herein is a soft-tissue augmenting kit including, in some embodiments, a syringe and the injectable composition formulated for augmenting one or more soft tissues of a human or animal. Also provided herein is a method for augmenting one or more soft tissues of a human or animal including, in some embodiments, injecting the injectable composition into the one or more soft tissues of the human or animal.

11 Claims, 4 Drawing Sheets

SYSTEM AND METHODS FOR SOFT-TISSUE AUGMENTATION

PRIORITY

This application is a continuation-in-part of, and claims the benefit of, U.S. patent application, entitled "System And Methods For Soft-Tissue Augmentation," filed on May 23, 2018, and having application Ser. No. 15/987,732, which claims the benefit of and priority to U.S. Provisional application, entitled "Soft-Tissue Augmentation System And Methods Thereof," filed on May 24, 2017, and having application Ser. No. 62/510,601.

FIELD

The field of the present disclosure generally relates to soft-tissue augmentation. More particularly, the field of the present disclosure relates to a system and methods for soft-tissue augmentation of the feet or other parts of the body.

BACKGROUND

A number of age-related pathologies develop as a result of atrophy of the soft tissues of the feet, including atrophy of the plantar fat pad. These conditions can be extremely painful, often leading to corns on the digits and calluses on the plantar aspect of the ball of the foot. In addition to the painful skin lesions, prolonged pressure against the resulting boney prominences can further break down the skin through ulceration, commonly leading to infection. These conditions can be much more serious in individuals suffering from peripheral vascular disease, diabetes, peripheral neuropathy, or a combination thereof. Provided herein, in some embodiments, are systems and methods for soft-tissue augmentation of the feet or other parts of the body.

SUMMARY

In an exemplary embodiment, provided herein, an injectable composition includes a soft-tissue augmenting agent and a vehicle for the soft-tissue augmenting agent formulated for augmenting one or more soft tissues of a human or animal.

In another exemplary embodiment, the soft-tissue augmenting agent includes a combination of saline and micronized dermis. In another exemplary embodiment, the soft-tissue augmenting agent includes a combination of hydrolyzed collagen and micronized dermis. In another exemplary embodiment, the soft-tissue augmenting agent further includes human- or animal-derived amino acids, polypeptides, cells, tissues, placentas, or a combination thereof. In another exemplary embodiment, the soft-tissue augmenting agent further includes synthetic amino acids, polypeptides, cells, tissues, or a combination thereof. In another exemplary embodiment, the soft-tissue augmenting agent further includes micronized silicone particles, acrylic beads, polyethylene, polyether ether ketone, other synthetics, or a combination thereof. In another exemplary embodiment, the vehicle includes water, saline, buffered saline, liquid collagen, silicone liquid, or a combination thereof.

In another exemplary embodiment, the injectable composition is formulated for augmenting soft tissue in a human plantar fat pad. In another exemplary embodiment, the injectable composition is formulated for augmenting soft tissue in a human hand. In another exemplary embodiment, the injectable composition is formulated for augmenting soft tissue in a human face.

In an exemplary embodiment, provided herein, a soft-tissue augmenting kit includes a syringe and an injectable composition formulated for augmenting one or more soft tissues of a human or animal. The syringe is configured for delivering the injectable composition to the one or more soft tissues of the human or animal. The injectable composition includes a soft-tissue augmenting agent and a vehicle for the soft-tissue augmenting agent.

In another exemplary embodiment, the soft-tissue augmenting agent includes a combination of saline and micronized dermis. In another exemplary embodiment, the soft-tissue augmenting agent includes a combination of hydrolyzed collagen and micronized dermis. In another exemplary embodiment, the soft-tissue augmenting agent further includes human- or animal-derived amino acids, polypeptides, cells, tissues, placentas, or a combination thereof. In another exemplary embodiment, the soft-tissue augmenting agent further includes synthetic amino acids, polypeptides, cells, tissues, or a combination thereof. In another exemplary embodiment, the soft-tissue augmenting agent further includes micronized silicone particles, acrylic beads, polyethylene, polyether ether ketone, other synthetics, or a combination thereof. In another exemplary embodiment, the vehicle includes water, saline, buffered saline, liquid collagen, silicone liquid, or a combination thereof.

In another exemplary embodiment, the injectable composition is provided in a single container configured for drawing the injectable composition into the syringe. In another exemplary embodiment, the soft-tissue augmenting agent is provided in a first container, the vehicle is provided in a second container, and the first container is configured for suspending or diluting the soft-tissue augmenting agent with the vehicle in the first container. In another exemplary embodiment, the soft-tissue augmenting kit further includes a targeting arm for the syringe and a marking pen.

In an exemplary embodiment, provided herein, a method for augmenting one or more soft tissues of a human or animal includes injecting an injectable composition into the one or more soft tissues of the human or animal. The injectable composition includes a soft-tissue augmenting agent and a vehicle for the soft-tissue augmenting agent. The soft-tissue augmenting agent includes a combination of saline and micronized dermis. In some embodiments, the soft-tissue augmenting agent includes a combination of hydrolyzed collagen and micronized dermis, and the vehicle includes water, saline, buffered saline, liquid collagen, silicone liquid, or a combination thereof.

In another exemplary embodiment, the method further includes drawing the injectable composition into a syringe before injecting the injectable composition into the one or more soft tissues of the human or animal. In another exemplary embodiment, the method further includes suspending or diluting the soft-tissue augmenting agent with the vehicle before drawing the injectable composition into the syringe.

In an exemplary embodiment, an injectable composition for augmenting one or more soft tissues of a human or an animal comprises: a soft-tissue augmenting agent; and a vehicle for the soft-tissue augmenting agent.

In another exemplary embodiment, the soft-tissue augmenting agent includes partially demineralized tissue. In another exemplary embodiment, the soft-tissue augmenting agent includes human- or animal-derived partially demineralized tissue. In another exemplary embodiment, the soft-tissue augmenting agent includes a first portion comprising demineralized bone and a second portion comprising mineralized hydroxyapatite. In another exemplary embodiment, the first portion comprises between about 20% to about 60% by volume of the soft-tissue augmenting agent. In another exemplary embodiment, the second portion comprises between about 40% to about 80% by volume of the soft-tissue augmenting agent.

In another exemplary embodiment, the soft-tissue augmenting agent and the vehicle are supplied together by way of a single syringe. In another exemplary embodiment, the vehicle includes water, saline, buffered saline, liquid collagen, silicone liquid, or a combination thereof. In another exemplary embodiment, the injectable composition is formulated for augmenting soft tissue in a human plantar fat pad. In another exemplary embodiment, the injectable composition is formulated for augmenting soft tissue in a human hand. In another exemplary embodiment, the injectable composition is formulated for augmenting soft tissue in a human face.

In an exemplary embodiment, a method for an injectable composition for augmenting one or more soft tissues of a human or an animal comprises: preparing a soft-tissue augmenting agent; forming a mixture comprising a vehicle and the soft-tissue augmenting agent; and supplying the mixture by way of a syringe for delivering the injectable composition to the one or more soft tissues of the human or animal.

In another exemplary embodiment, preparing includes combining a first portion comprising demineralized bone and a second portion comprising mineralized hydroxyapatite. In another exemplary embodiment, combining includes portioning the first portion to comprise between about 20% to about 60% by volume of the soft-tissue augmenting agent. In another exemplary embodiment, combining includes portioning the second portion to comprise between about 40% to about 80% by volume of the soft-tissue augmenting agent.

In another exemplary embodiment, supplying includes combining the vehicle and the soft-tissue augmenting agent in a single syringe. In another exemplary embodiment, forming the mixture includes providing the vehicle comprising any of water, saline, buffered saline, liquid collagen, silicone liquid, or a combination thereof.

These and other features of the concepts provided herein may be better understood with reference to the drawings, description, and appended claims.

BRIEF DESCRIPTION OF THE DRAWINGS

The drawings refer to embodiments of the present disclosure in which.

Figure 1A:
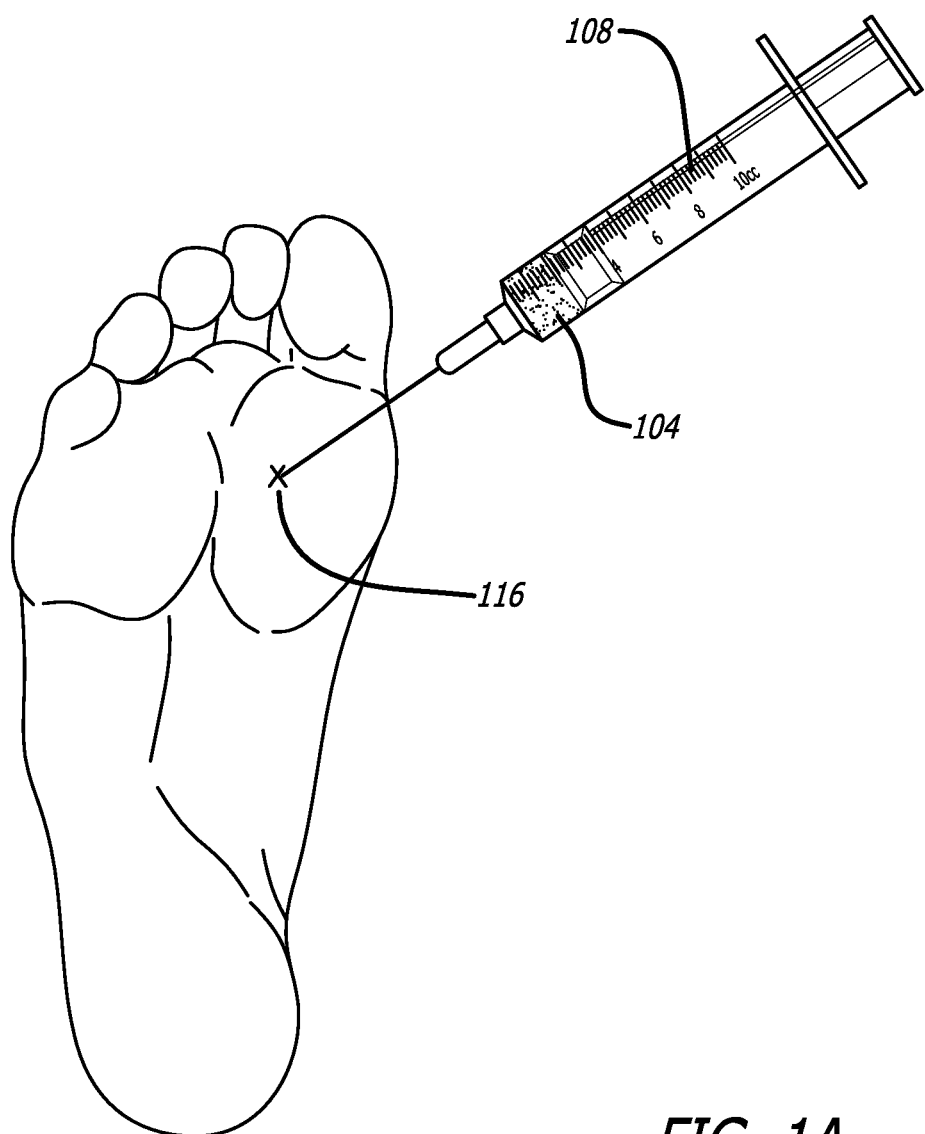
FIG. 1A is a schematic illustrating an exemplary embodiment of an injectable composition in a syringe for augmenting one or more soft tissues of a human or animal in accordance with the present disclosure.

While the present disclosure is subject to various modifications and alternative forms, specific embodiments thereof have been shown by way of example in the drawings and will herein be described in detail. The invention should be understood to not be limited to the particular forms disclosed, but on the contrary, the intention is to cover all modifications, equivalents, and alternatives falling within the spirit and scope of the present disclosure.

DETAILED DESCRIPTION

Before some particular embodiments are provided in greater detail, it should be understood that the particular embodiments provided herein do not limit the scope of the concepts provided herein. It should also be understood that a particular embodiment provided herein can have features that can be readily separated from the particular embodiment and optionally combined with or substituted for features of any of a number of other embodiments provided herein.

Regarding terminology used herein, it should also be understood the terminology is for the purpose of describing some particular embodiments, and the terminology does not limit the scope of the concepts provided herein. Unless indicated otherwise, ordinal numbers (e.g., first, second, third, etc.) are used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. It should also be understood that, unless indicated otherwise, any labels such as "left," "right," "front," "back," "top," "bottom," "forward," "reverse," "clockwise," "counter clockwise," "up," "down," or other similar terms such as "upper," "lower," "aft," "fore," "vertical," "horizontal," "proximal," "distal," and the like are used for convenience and are not intended to imply, for example, any particular fixed location, orientation, or direction. Instead, such labels are used to reflect, for example, relative location, orientation, or directions. It should also be understood that the singular forms of "a," "an," and "the" include plural references unless the context clearly dictates otherwise.

Unless defined otherwise, all technical and scientific terms used herein have the same meaning as commonly understood by those of ordinary skill in the art.

A number of age-related pathologies develop as a result of atrophy of the soft tissues of the feet, including atrophy of the plantar fat pad. These conditions can be extremely painful, often leading to corns on the digits and calluses on the plantar aspect of the ball of the foot. In addition to the painful skin lesions, prolonged pressure against the resulting boney prominences can further break down the skin through ulceration, commonly leading to infection. These conditions can be much more serious in individuals suffering from peripheral vascular disease, diabetes, peripheral neuropathy, or a combination thereof. Provided herein, in some embodiments, are systems and methods for soft-tissue augmentation of the feet or other parts of the body.

For example, a preventive therapy is provided, in some embodiments, for patients suffering from the foregoing foot related pathologies. Such a therapy includes an injectable composition for the soft tissues or the plantar fat pad of the foot that replaces the atrophied fatty tissue. Not only does such a therapy minimize a progression of the foregoing foot related pathologies, but such a therapy relieves pain as well.

Figure 1B:
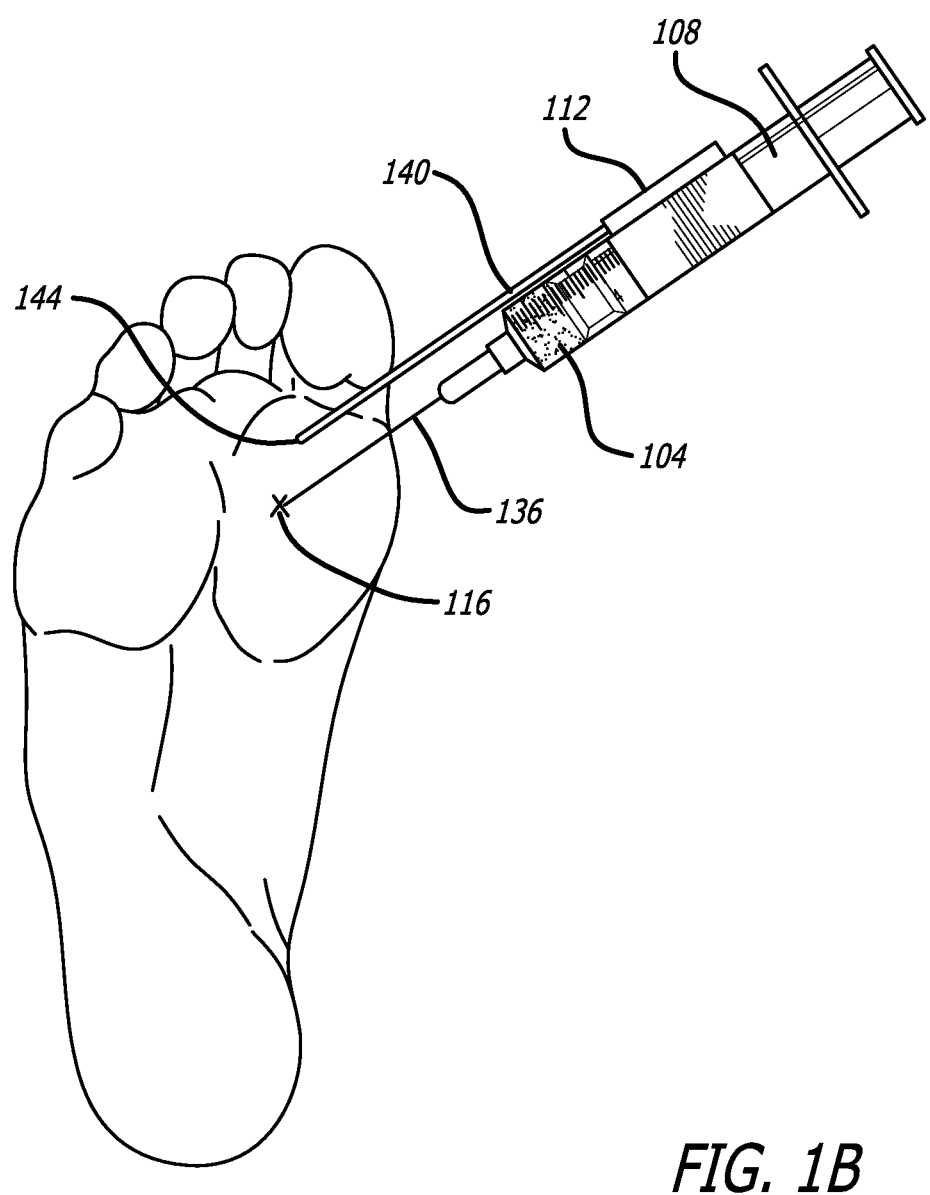
FIG. 1B is a schematic illustrating an exemplary embodiment of an injectable composition in a syringe with a targeting arm for augmenting one or more soft tissues of a human or animal in accordance with the present disclosure.

FIGS. 1A and 1B are schematics illustrating an injectable composition 104 in a syringe 108 for augmenting one or more soft tissues of a human or animal in accordance with some embodiments. FIG. 1B additionally provides a targeting arm 112 for the syringe 108. While the soft-tissue augmenting injectable composition 104 is shown in relation to augmenting soft tissue of a plantar foot pad 116, it should be understood that the injectable composition 104 is not limited thereto. The injectable composition 104 can be formulated to augment any one or more soft tissues of a human or animal, without limitation. For example, the injectable composition 104 may be formulated for augmenting soft tissue in a human hand or face.

In general, the soft-tissue augmenting injectable composition 104 includes, but is not limited to, a soft-tissue augmenting agent and a vehicle for the soft-tissue augmenting agent. The soft-tissue augmenting agent includes a combination of saline and micronized dermis. In some embodiments, the soft-tissue augmenting agent may include a combination of hydrolyzed collagen and micronized dermis. The soft-tissue augmenting agent may further include human- or animal-derived amino acids, polypeptides (e.g., proteins such as human-serum albumin ["HSA"], bovine-serum albumin ["BSA"], etc.), cells (e.g., stem cells), tissues (e.g., allografts or xenografts), placentas, or a combination thereof. Additionally or alternatively, the soft-tissue augmenting agent can further include synthetic amino acids, polypeptides, cells, tissues, or a combination thereof. Additionally or alternatively, the soft-tissue augmenting agent can further include micronized (e.g., micron sized), powdered, or pulverized silicone particles, acrylic beads, polyethylene, polyether ether ketone, other synthetics, or a combination thereof.

Moreover, in some embodiments, the soft-tissue augmenting agent may include human- or animal-derived partially demineralized tissue. For example, in some embodiments, the soft-tissue augmenting agent may include a first portion comprising demineralized bone and a second portion comprising mineralized hydroxyapatite. In some embodiments, the portion of demineralized comprises between about 20% to about 60% by volume of the soft-tissue augmenting agent. Further, in some embodiments, the portion of mineralized hydroxyapatite comprises between about 40% to about 80% by volume of the soft-tissue augmenting agent.

The vehicle for the soft-tissue augmenting agent can include water, saline, buffered saline (e.g., phosphate-buffered saline), liquid collagen (e.g., hydrolyzed collagen in water, saline, buffered saline, etc.), silicone liquid, or a combination thereof.

The soft-tissue augmenting injectable composition 104 may be provided in a soft-tissue augmenting kit including one or more additional components for augmenting one or more soft tissues of a human or animal. Each additional component of the one or more additional components can include, but is not limited to, a needle (e.g., a needle with a gauge sufficient for injecting the injectable composition without occlusion thereof and significant pain to a patient, such as 20 gauge or smaller), one or more syringes (e.g., a syringe including a plunger and a graduated barrel for measuring an amount of the injectable composition 104), a targeting arm for syringes, a syringe connector, an ampoule, and a marking pen. The injectable composition 104 and the optional one or more additional components of the soft-tissue augmenting kit may be sterile for immediate use upon unpacking the soft-tissue augmenting kit.

Figure 2A:
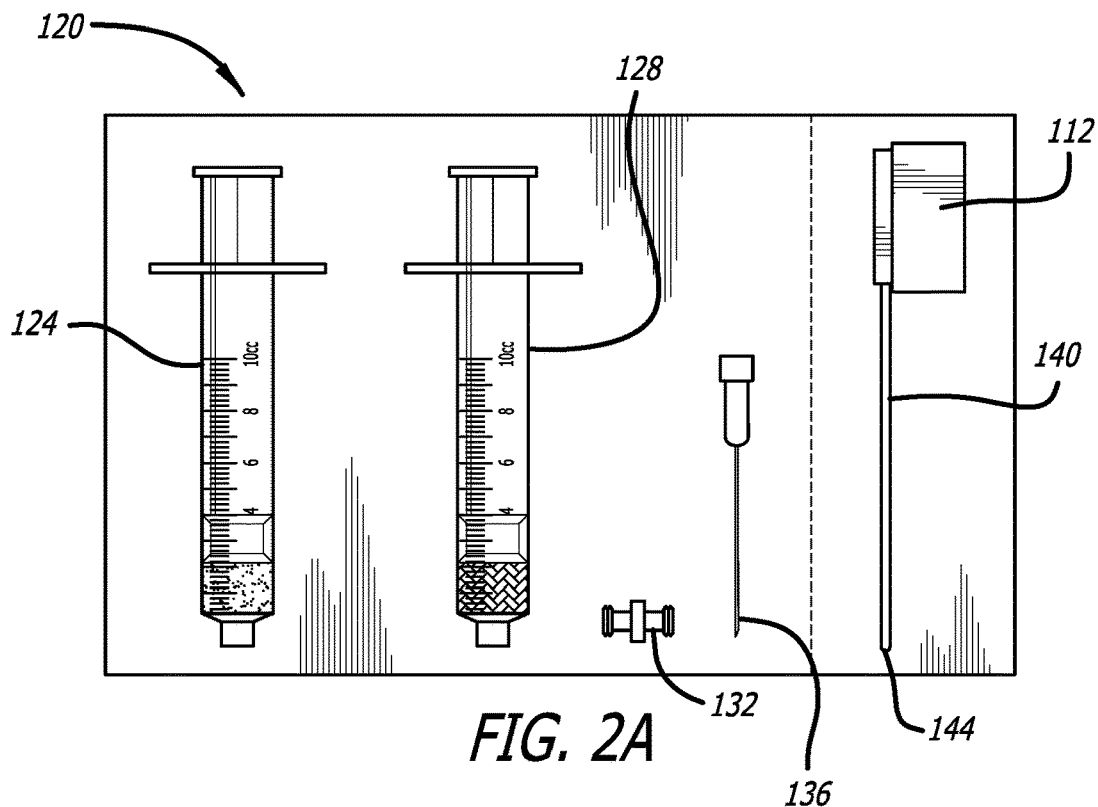
FIG. 2A is a schematic illustrating an exemplary embodiment of a soft-tissue augmenting kit including a syringe with an injectable composition in accordance with the present disclosure.

FIG. 2A is a schematic illustrating an exemplary embodiment of a soft-tissue augmenting kit 120 that includes a first syringe 124 and a second syringe 128. Either of the first and second syringes 124, 128 may be pre-filled with a soft-tissue augmenting agent and the other of the syringes may be pre-filled with a vehicle for the soft-tissue augmenting agent. An optional syringe connector 132 may be included in the soft-tissue augmenting kit 120 and configured to facilitate coupling the first syringe 124 with the second syringe 128. The syringe connector 132 may be any suitable connector for placing the first syringe 124 into fluid communication with the second syringe 128, such as a female-to-female Luer Lock connector. During coupling the first and second syringes 124, 128, the soft-tissue augmenting agent may be mixed with the vehicle for the soft-tissue augmenting agent thereby forming the injectable composition 104 for delivery to the one or more soft tissues of the human or animal.

Once mixed, the injectable composition 104 may be retained in either of the first and second syringes 124, 128 (e.g., syringe 124) prior to delivery to the human or animal. Upon being coupled with a needle 136, which may also be included in the soft-tissue augmenting kit 120, the syringe 124 may be configured for delivering the injectable composition 104 to the one or more soft tissues of the human or animal. It is contemplated, however, that in some embodiments, the soft-tissue augmenting kit 120 may be implemented with a single syringe 124 that is filled with a pre-mixed portion of the injectable composition 104, thereby obviating a step of manually mixing the soft-tissue augmenting agent with the vehicle as described hereinabove.

Also shown in FIG. 2A is an optional targeting arm 112 configured to snap onto a barrel of the syringe 124 as shown in FIG. 1B. The targeting arm 112 may include a longitudinal member 140 parallel to and extending in a same direction as the needle 136 when the targeting arm 112 and the needle 136 are both connected to the syringe 124. The longitudinal member 140 can have a fixed length in the targeting arm 112 useful in controlling an injection depth for an injection of the injectable composition 104 with the syringe 124. The targeting arm 112 can be configured to snap onto the barrel of the syringe 124 at a particular location on the barrel such that a distal end 144 of the longitudinal member 140 is short of the needle 136 in correspondence with a recommended injection depth. The targeting arm 112 can also be configured to snap onto the barrel of the syringe 124 at any desired location on the barrel such that the distal end 144 of the longitudinal member 140 is short of the needle 136 in correspondence with a desired injection depth. For example, a leading or trailing edge of the targeting arm 112 around the barrel of the syringe 124 may be adjusted per graduations on the barrel such that the distal end 144 of the longitudinal member 140 is short of the needle 136 in correspondence with the desired injection depth.

Figure 2B:
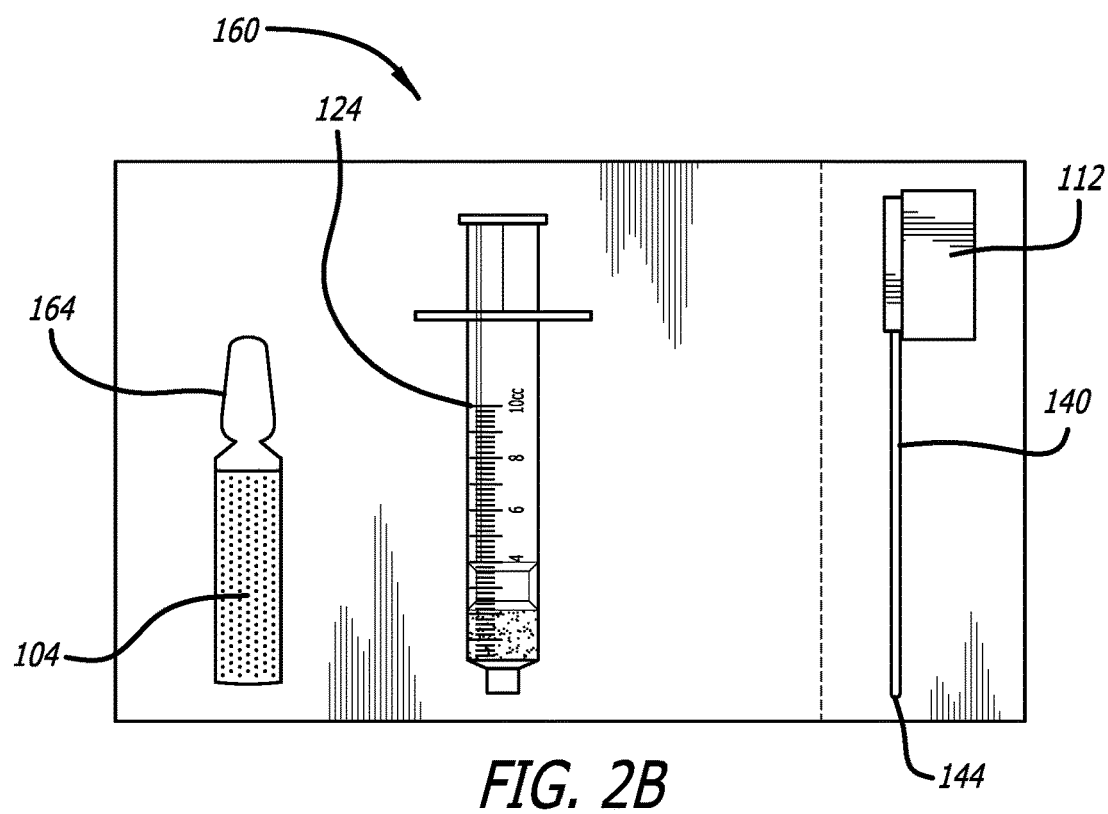
FIG. 2B is a schematic illustrating an exemplary embodiment of a soft-tissue augmenting kit including a syringe and a container with an injectable composition in accordance with the present disclosure.

FIG. 2B is a schematic illustrating an exemplary embodiment of a soft-tissue augmenting kit 160 including a syringe 124 and a container with the injectable composition 104 in accordance with the present disclosure. As shown, the container is comprised of an ampoule 164 that is filled with the injectable composition 104 formulated for augmenting one or more soft tissues of a human or animal. Upon coupling the syringe 124 with a needle, such as the needle 136 which may also be included in the soft-tissue augmenting kit 160, the syringe 124 can be configured for drawing the injectable composition 104 into the syringe from the ampoule 164 and subsequently delivering the injectable composition to the one or more soft tissues of the human or animal.

Also shown in FIG. 2B the soft-tissue augmenting kit 160 may further include an optional targeting arm 112 that is configured to snap onto a barrel of the syringe 124 as shown in FIG. 1B and discussed in connection with FIG. 2A.

Figure 2C:
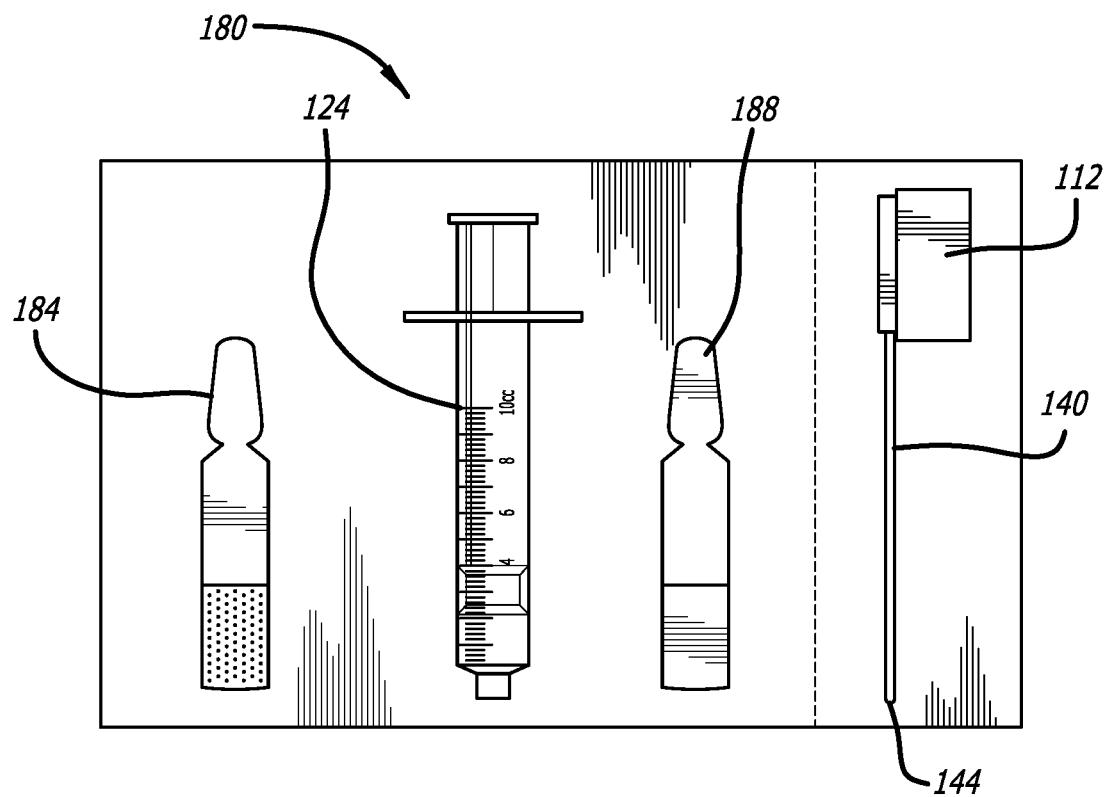
FIG. 2C is a schematic illustrating an exemplary embodiment of a soft-tissue augmenting kit including a syringe, a first container with a soft-tissue augmenting agent, and a second container with a vehicle for a soft-tissue augmenting agent in accordance with the present disclosure.

FIG. 2C is a schematic illustrating an exemplary embodiment of a soft-tissue augmenting kit 180 that includes a syringe 124, a first ampoule 184 that is pre-filled with a soft-tissue augmenting agent, and a second ampoule 188 that is pre-filled with a vehicle for the soft-tissue augmenting agent. Upon coupling the syringe 124 with a needle, such as the needle 136 which may also be included in the soft-tissue augmenting kit 180, the syringe 124 can be configured for drawing the vehicle into the syringe 124 from the second ampoule 188 and subsequently delivering the vehicle to the first ampoule 184, thereby mixing the agent and the vehicle within the first ampoule to form the injectable composition 104. Once the vehicle and the agent are suitably mixed, the resulting injectable composition 104 may be drawn into the syringe 124 from the first ampoule 184 and subsequently delivered to the one or more soft tissues of the human or animal as discussed hereinabove.

Also shown in FIG. 2C the soft-tissue augmenting kit 180 may further include an optional targeting arm 112 that is configured to snap onto a barrel of the syringe 124 as shown in FIG. 1B and discussed in connection with FIG. 2A.

Methods for augmenting one or more soft tissues of a human or animal include, in some embodiments, injecting the injectable composition 104 into one or more soft tissues of the human or animal. The injectable composition 104 includes the soft-tissue augmenting agent and the vehicle for the soft-tissue augmenting agent.

The methods can further include drawing the injectable composition 104 into a syringe 124 before injecting the injectable composition into the one or more soft tissues of the human or animal. However, in some embodiments, the syringe 124 may be pre-filled with the injectable composition 104 in a soft-tissue augmenting kit, thereby obviating such a step of drawing the injectable composition into the syringe.

The methods can further include coupling together a first syringe 124 that is pre-filled with a soft-tissue augmenting agent and a second syringe 128 that is pre-filled with a vehicle for the soft-tissue augmenting agent, drawing the vehicle into the first syringe 124 from the second syringe 128, and mixing the vehicle and the agent in the first syringe 124 to form the injectable composition 104. In some embodiments, the first syringe 124 and the second syringe 128 may be coupled by way of the optional syringe connector 132.

The methods can further include suspending or diluting the soft-tissue augmenting agent with the vehicle to form the injectable composition 104 before drawing the injectable composition into the syringe 124 for injection. However, in some embodiments, an ampoule 164 or the syringe 124 in a soft-tissue augmenting kit may include the injectable composition 104, thereby obviating such a step of forming the injectable composition.

While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. To the extent there are variations of the invention, which are within the spirit of the disclosure or equivalent to the inventions found in the claims, it is the intent that this patent will cover those variations as well. Therefore, the present disclosure is to be understood as not limited by the specific embodiments described herein, but only by scope of the appended claims.

What is claimed is:

1. A soft-tissue augmenting kit comprising:
   an injectable composition for augmenting one or more soft tissues of a human or an animal, comprising:
   a soft-tissue augmenting agent; and
   a vehicle for the soft-tissue augmenting agent; and
   a targeting arm that snaps onto a barrel of a syringe, the targeting arm comprising a longitudinal member that is parallel to and extending in a same direction as the needle when the targeting arm and the needle are both coupled to the syringe; and
   wherein the longitudinal member comprising a fixed length in the targeting arm to control an injection depth for an injection of the injectable composition with the syringe.

2. The soft-tissue augmenting kit of claim 1, wherein the soft-tissue augmenting agent includes partially demineralized tissue.

3. The soft-tissue augmenting kit of claim 2, wherein the soft-tissue augmenting agent includes human- or animal-derived partially demineralized tissue.

4. The soft-tissue augmenting kit of claim 2, wherein the soft-tissue augmenting agent includes a first portion comprising demineralized bone and a second portion comprising mineralized hydroxyapatite.

5. The soft-tissue augmenting kit of claim 4, wherein the first portion comprises between about 20% to about 60% by volume of the soft-tissue augmenting agent.

6. The soft-tissue augmenting kit of claim 4, wherein the second portion comprises between about 40% to about 80% by volume of the soft-tissue augmenting agent.

7. The soft-tissue augmenting kit of claim 1, wherein the soft-tissue augmenting agent and the vehicle are supplied together by way of a single syringe.

8. The soft-tissue augmenting kit of claim 7, wherein the vehicle includes water, saline, buffered saline, liquid collagen, silicone liquid, or a combination thereof.

9. The soft-tissue augmenting kit of claim 8, wherein the injectable composition is formulated for augmenting soft tissue in a human plantar fat pad.

10. The soft-tissue augmenting kit of claim 8, wherein the injectable composition is formulated for augmenting soft tissue in a human hand.

11. The soft-tissue augmenting kit of claim 8, wherein the injectable composition is formulated for augmenting soft tissue in a human face.

* * * * *